United States Patent [19]

Miller, Jr.

[11] 4,115,586
[45] Sep. 19, 1978

[54] ANTIHYPERTHERMIC USE FOR PROSTAGLANDINS

[75] Inventor: William L. Miller, Jr., Kalamazoo, Mich.

[73] Assignee: The Upjohn Company, Kalamazoo, Mich.

[21] Appl. No.: 816,398

[22] Filed: Jul. 18, 1977

[51] Int. Cl.$^2$ .................. A61K 31/19; A61K 31/215
[52] U.S. Cl. ..................................... 424/317; 424/305
[58] Field of Search ................................ 424/305, 317

[56] References Cited
PUBLICATIONS

Upjohn Prostaglandin Bibliography, Nov. 6, 1969 & Supplement pp. 1970-22 & 1972-42.

*Primary Examiner*—Sam Rosen
*Attorney, Agent, or Firm*—Robert A. Armitage

[57] ABSTRACT

The present invention provides a method whereby pyrogen-induced, prostaglandin-induced and idiopathic fever is alleviated by systemic administration of a hypothermic prostaglandin.

The hypothermic prostaglandins of the present invention are ω-aryl-PGF-type compounds, e.g., 15-methyl-17-phenyl-ω-trinor-PGF$_{2\alpha}$ and 16-phenoxy-ω-tetranor-PGF$_{2\alpha}$.

9 Claims, No Drawings

ANTIHYPERTHERMIC USE FOR PROSTAGLANDINS

BACKGROUND OF THE INVENTION

Amelioration and elimination of fever are important therapeutic endpoints in the treatment of a wide variety of undesirable physiological conditions. The present invention provides a method whereby fever (i.e., elevated body temperature) is reduced or eliminated in humans by systemic administration of certain hypothermic prostaglandins. In particular, ω-aryl-PGF$_\alpha$-type compounds are disclosed herein as hypothermic prostaglandins capable of reducing or eliminating fever in a dose-response manner.

Human thermo-regulatory function is centered in the hypothalamus and both hypothermic (temperature lowering) and hyperthermic (temperature raising) substances are known to interplay in the control of body temperature. See, for example, Proceedings of the Royal Society of London, Bulletin 191:199-229 (1975) and Karim, S.S.M., Ed., Prostaglandin Physiological Pharmacological and Pathological Aspects, MTP Press, Ltd., Lancaster, U.K. (1975) pages 13-17, for a discussion of the interplay of certain monoamines (i.e., 5-hydroxytryptamine and norepinephrine) and acetylcholine.

The above references not only describe pyrogen induction of fever and idiopathic fever, but further describe "prostaglandin fever," characteristically induced by administration of prostaglandin E$_1$ and related compounds. See Veale, et al., Pharmacology, Biochemistry and Behavior, 4:143-150 (1976).

Further evidence for the pyretic effects of prostaglandin E$_1$ are suggested by the characteristic of known antipyretic agents as further being inhibitors of prostaglandin synthetase. See, for example, the references cited in Karim, indicating that pyrogen-induced fever is susceptible to treatment with antipyretic prostaglandin synthetase inhibitors, while fever induced by exogenous prostaglandin administration is not.

SUMMARY OF THE INVENTION

The present invention comprises a method of preventing or ameliorating, eliminating, or reducing fever in a human suffering from fever or susceptible to fever development, such susceptibility being by virtue of pyrogen or fever-inducing prostaglandin challenge, which comprises administering a hypothermic dose of a hypothermic prostaglandin (hypothermic-PG).

Hypothermic-PG's are those prostaglandin analogs of the formula:

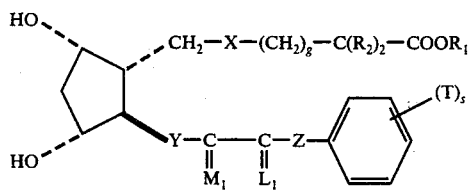

wherein X is cis—CH=CH—CH$_2$—, cis—CH$_2$—CH=CH—, or —(CH$_2$)$_3$— and Y is trans—CH=CH— or X is—(CH$_2$)$_3$— and Y is —CH$_2$CH$_2$—;
wherein R$_2$ is hydrogen or fluoro;
wherein g is one, 2, or 3;
wherein Z is oxa or —(CH$_2$)$_h$—, wherein h is zero, one, 2, or 3;
wherein M$_1$ is

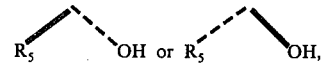

wherein R$_5$ is hydrogen or methyl;
wherein L$_1$ is

or a mixture or

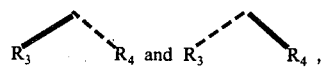

wherein R$_3$ and R$_4$ are hydrogen, methyl, or fluoro, being the same or different;
wherein g is zero, one, or 2 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl; and
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

Particularly preferred compounds for potency of hypothermic response are those compounds wherein R$_2$, R$_3$, and R$_4$ are all hydrogen and R$_1$ is hydrogen, lower alkyl, or a cation. Accordingly, the preferred hypothermic PG's include
  16-phenoxy-ω-tetranor-PGF$_2\alpha$, methyl ester;
  15-methyl-17-phenyl-ω-trinor-PGF$_2\alpha$, methyl ester;
  16-(m-trifluoromethyl)phenoxy-ω-tetranor-PGF$_2\alpha$;
  17-phenyl-ω-trinor-PGF$_2\alpha$, ethyl ester; and the like.

For a description of the preparation of the various hypothermic-PG's and their manner of formulation for pharmaceutical purposes, see
  U.S. Pat. No 4,001,300;
  U.S. Pat. No. 3,987,087;
  Belgium Pat. No. 806,995, abstracted at Derwent Farmdoc CPI No. 38269V/21; and
  Netherlands Pat. No 7,306,462, abstracted at Derwent Farmod CPI No. 73279U-B.

For the purposes of the present method, any convenient systemic form of administration is employed. See, for examle, the routes of administration and dosage regimens described in the above references.

Further with respect to the above method, both prophylactic (i.e., prevention and amelioration) and therapeutic (elimination or reduction) of fever is within the scope of the present invention.

For the therapeutic use, the hypothermic-PG is administered in a dose sufficient to either reduce or eliminate fever, thereby returning body temperature of a patient to normal, regardless of the cause of the fever, whether known or unknown. Accordingly, the present method is effective in treating fever induced by pyrogens or prostaglandin treatment, or idiopathic fever.

In the prophylaxis of fever, the hypothermic-PG is administered either concomitantly with exposure to the known pyrogen or at the earliest convenience after exposure to a pyrogen. Contemplated within the prophylactic use of the present method are pyrogens of the various types and categories known to the art, but particularly include viral pathogens, e.g., influenza viruses and common cold viruses. Further, the present method contemplates reduction or elimination of fever when prostaglandin compounds, particularly PGE-type compounds are administered for any pharmacological purpose. Such E-type prostaglandins (e.g., $PGE_1$) are known to induce fever when used pharmaceutically (e.g., labor induction) and accordingly the present hypothermic-PG is administered concomitantly with or subsequent to prostaglandin therapy, thereby eliminating hyperthermia as a side effect of the fever-inducing prostaglandin treatment.

With respect to dosages of the hypothermic-PG when used in response to prostaglandin fever, the dosage of both the hypothermic-PG and other PG's should be titrated, taking into account the contribution of the hypothermic-PG to the desired therapeutic action of the other prostaglandin-type compound being administered. See, for example, the cited references above describing the wide spectrum of biological actions which are known for the present hypothermic-PG's and the dosages at which such biological actions are exhibited.

With regard to dosages at which the present invention operates, a hypothermic dose is administered such that the body temperature of the patient being treated decreases in an amount less than or equal to the difference between the patient's normal body temperature and the fever temperature. When employing the present invention prophylactically, an estimation is made of the expected hyperthermic response to the pyrogen or prostaglandin challenge, and the hypothermic dose determined accordingly.

While dosages will vary widely depending upon the size, weight, and condition of the patient, as well as the route of administration selected, dosages particularly about 10 to 100 μg. per kg., but in no event greater than 500 μg. per kg. are employed according to the present method when a subcutaneous route of administration is selected. Since the response of the patient to a hypothermic-PG may be rapid and prolonged, several small doses may be administered sequentially, providing incremental reductions in the patient's temperature until the desired endpoint of temperature reduction is achieved.

In many cases, for example, complete elimination of fever (i.e., return of body temperature to normal) is not a necessary clinical endpoint, and accordingly fever is reduced by less than the amount necessary to return the body to a normal temperature, but by the amount which the attending physician determines to be the necessary and appropriate clinical endpoint to avoid the untoward effects of high fever. Accordingly the present invention provides for both the total abolition of fever (i.e., prevention or elimination) or the more conservative approach in merely reducing fever from undesirably high temperature levels (i.e., amelioration or reduction). As used herein the term "hypothermic" dose thus includes both concepts of dose sufficient to prevent or eliminate and ameliorate or reduce fever.

A particular advantage of the present invention resides in the ability of the hypothermic-PG, particularly the preferred hypothermic-PG's herein, to achieve control of the patient's fever at dosages significantly below those at which the previously reported therapeutic actions for these compounds are observed. Thus, for example, 17-phenyl-ω-trinor-$PGF_2α$ exhibits good fever control at dosages several times less than those required for its use in pregnancy interruption. The invention herein thus provides a facile and simple method for fever control using prostaglandin analogs in a manner which yields highly selective therapeutic action, therby eliminating or reducing the incidence of side effects often associated with the clinical use of the present hyperthermic-PG's for other purposes.

A convenient demonstration of the operation of the present method in non-fevered primates (Rhesus monkeys). which further provides a convenient method for assessing the potency of the hypothermic-PG's herein, comprises a telemetric method of measuring and recording abdominal core temperature in Rhesus monkeys containing surgically implanted radio-telemeters which contain equipment for sensitive measurement of core temperatures. Accordingly, the core temperatures of such animals with temperature measuring radio-telemeters are able to be determined in unrestricted and unanesthetized animals. Further, automatic, continuous recording of the telemetric signals enables a convenient record to be obtained. See Mackay, R. Stuart, Bio-Medical Telemetry, Chapter 11, 2nd Edition, John Wiley & Sons, Inc., New York City, 1970. Telemetry data on monkeys equipped in this manner and given subcutaneous doses of hypothermic-PG's is reported in Tables 1 and 2. As is readily apparent, temperature reductions of about 2°–3° C. (e.g., 3½° to 5½° F.) are obtained.

Moreover, significant temperature reduction is observed for 3–5 hr. as a result of the single dose of hypothermic-PG.

Table 1

| Effect of 17-phenyl-ω-trinor-$PGF_2α$ on Rhesus Monkey Core Temperature | | |
|---|---|---|
| Monkey | Peak Temperature Decrease (° C) | Duration (hr)* |
| 1 | 1.3 | 2.50 |
| 2 | 2.5 | 5.00 |
| 3 | 1.3 | 2.00 |
| 4 | 2.3 | 4.00 |
| 5 | 1.3 | 1.50 |
| 6 | 2.0 | 4.50 |
| 7 | 1.2 | 1.80 |
| 8 | 2.2 | 2.50 |
| Mean | 1.76 (3.2° F) | 2.97 |

Dose: 60 μg/kg subcutaneous
*Time of significant temperature reduction

Table 2

| Effect of 16-phenoxy-ω-tetranor-$PGF_2α$ on Rhesus Monkey Core Temperature | | |
|---|---|---|
| Monkey | Peak Temperature Decrease (°0 C) | Duration (hr)* |
| 1 | 2.9 | 3.00 |
| 2 | 4.2 | 6.50 |
| 3 | 2.6 | 7.50 |
| 4 | 3.5 | 5.00 |
| 5 | 2.4 | 5.50 |
| 6 | 3.2 | 5.50 |
| 7 | 1.6 | 2.30 |
| 8 | 3.3 | 5.50 |
| Mean | 2.96 (5.3° F) | 5.10 |

Dose: 20 μg/kg subcutaneous
*Time of significant temperature reduction

I claim:

1. A method of preventing or ameliorating fever in a human susceptible to fever development, such susceptibility being by virtue of pyrogen or fever-inducing prostaglandin challange, which comprises administering a hypothermic dose of a hypothermic-prostaglandin (hypothermic-PG) to ameliorate said fever or administering prior to said challenge to prevent said fever.

2. A method according to claim 1, wherein the patient is susceptible to fever development by virtue of pyrogen challenge or exposure.

3. A method according to claim 1, wherein the patient is susceptible to fever development by virtue of fever-inducing prostaglandin challange.

4. A method according to claim 3, wherein the fever-inducing prostaglandin challenge comprises administration of 15-methyl-$PGE_2$ or its esters.

5. A method according to claim 3, wherein the fever-inducing prostaglandin challenge comprises administration of $PGE_2$ or its esters.

6. A method of eliminating or reducing fever in a human suffering from fever which comprises administering a hypothermic dose of a hypothermic-prostaglandin (hypothermic-PG).

7. A method according to claim 6, wherein by hypothermic dose of the hypothermic-PG is selected so as to eliminate fever.

8. A method according to claim 6, wherein the hypothermic dose of the hypothermic-PG is selected so as to reduce fever.

9. A method according to claim 6, wherein the fever is pyrogen-induced.

* * * * *